United States Patent [19]

Tardy et al.

[11] Patent Number: 4,931,546
[45] Date of Patent: Jun. 5, 1990

[54] PROCESS FOR THE TREATMENT OF COLLAGEN, NOTABLY FOR FACILITATING ITS CROSS-LINKING, AND THE COLLAGEN OBTAINED BY THE APPLICATION OF THE SAID PROCESS

[75] Inventors: Michel Tardy, Lyons; Jean-Louis Tayot, La Tour de Salvagny, both of France

[73] Assignees: Imedex; Institut Merieux, both of Lyons, France

[21] Appl. No.: 72,368

[22] Filed: Jul. 13, 1987

[30] Foreign Application Priority Data

Jul. 11, 1986 [FR] France ............................. 86 10160

[51] Int. Cl.$^5$ ............................................. C08H 1/06
[52] U.S. Cl. ................................................. 530/356
[58] Field of Search ........................... 530/356; 514/21

[56] References Cited

U.S. PATENT DOCUMENTS 4,280,954  7/1981  Yannas et al. ...................... 530/395

OTHER PUBLICATIONS

Eyre, Dr. et al., Biochem. Biophys. Res. Comm., 1973, vol. 52, No. 2, pp. 663–671.

Primary Examiner—Howard E. Schain
Assistant Examiner—Choon P. Koh
Attorney, Agent, or Firm—Larson and Taylor

[57] ABSTRACT

Collagen is submitted to a controlled oxidation by treatment with a solution of periodic acid or of a periodate, notably of sodium. Application to gels, implants, lenses, films, spheres, etc., of collagen.

26 Claims, No Drawings

PROCESS FOR THE TREATMENT OF COLLAGEN, NOTABLY FOR FACILITATING ITS CROSS-LINKING, AND THE COLLAGEN OBTAINED BY THE APPLICATION OF THE SAID PROCESS

The present invention concerns a process for the treatment of collagen with a view, notably, to facilitating its reticulation (i.e. cross-linking), and permitting the obtaining of a reticulated collagen with improved stability and mechanical characteristics.

In its medical and biomedical uses, collagen needs to respond to very rigorous mechanical, physio-chemical and biological requirements.

One of the limitations in the use of collagen resides in its often insufficient resistance to biodegradation and in its weak mechanical characteristics rendering its manipulation difficult.

The biodegradability of collagen depends essentially on its degree of reticulation and on the manner in which the reticulation was accomplished. It may vary from a few days for an uncured collagen to several months for a highly reticulated collagen. This reticulation permits the introduction of a certain number of inter- and intra-chain cross-linkages, in order to decrease the solubility of collagen.

The reticulation of collagen may be accomplished either by chemical means using curing agents such as glutaraldehyde or formaldehyde, or again diisocyanate, or by physical agents such as gamma, beta or ultraviolet radiation. But this latter method is complicated and aside from the reticulations can also cause breaks.

Treatment with glutaraldehyde, which is the treatment the most often used to cross-link collagen and which consists of immersing powders, films, gels or more or less concentrated solutions of collagen into a solution of glutaraldehyde, presents a certain number of disadvantages in certain applications. The introduction of glutaraldehyde into an aqueous collagen structure (gel or sponge) leads to the formation of very high molecular weight glutaraldehyde polymers which are difficult to eliminate by simple washing and may hydrolyze and cause a release of glutaraldehydes or remain in situ and find themselves liberated after the disappearance of the collagenic part.

Equally, collagen treated by a specific oxidase has already been reticulated, but such a treatment is expensive and particularly delicate, and can only be carried out under very special conditions (difficulty in the elimination of the lysyl oxidase at the end of the treatment).

The present invention aims to remedy the aforesaid disadvantages by proposing a process for the treatment of collagen permitting reticulation or cross-linking in a homogenous fashion in the collagen mass without the covalent addition of chemical reagents.

One of the goals of the invention is to provide collagen gels homogenously reticulated and of a high degree of stability.

Another aim of the invention is to provide a much more flexible process for the reticulation of collagen permitting, first, the introduction of a controlled oxidation of the collagen without triggering a great deal of reticulation (by modifying the pH; more acid range) and, second, by neutralization or alkalization of the pH, to trigger a reticulation at will of the collagen molecules.

Another aim of the invention is to provide stable powders or films of collagen having improved characteristics, notably of insolubility, even at acid pH.

Yet another aim of the invention is to provide powders or films of collagen having, on the surface, reactive groups permitting the coupling of collagen with biologically active molecules.

The process of collagen treatment conforming to the invention is characterized in that consists of submitting the collagen to a controlled oxidation by treatment with a periodic acid solution or with a periodate, notably of sodium.

The periodate treatment may be carried out either on collagen solutions or on already constituted gels, or again on films or on powders.

When the periodate treatment is carried out on collagenic solutions in anticipation of the preparation of gels, a solution of periodic acid or of a corresponding salt, notably sodium periodate, up to a concentration of 0,0001M to 0.1M, is added to the collagen solution the concentration of which in collagen is generally between 0.1 and 20%; the pH, which may be between 2 and 8, being advantageously acid at first, then neutral or basic after, which rapidly leads to the formation of an insoluble gel in a large pH range, including at acid pH, where before this treatment the collagen was soluble.

The excess aldehyde groups formed on the collagen molecule are neutralized, for example by a solution of glycine, ethanolamine, and/or sodium hydroboride, or used for the linking of proteins, fibronectin, growth factors, glycosaminoglycans, enzymes, bacteriocidal or bacteriostatic agents, antibiotics or any other product permitting a better biocompatibility and a greater resistance to biodegradation.

Periodate treatment might be complemented by a surface curing either by a solution of $NaIO_4$, or by a solution of di- or polyaldehyde.

A surface curing is obtained afterwards, if necessary, by treating the collagen gel with a solution of periodic acid or of sodium periodate or by a solution of di- or polyaldehyde the concentration of which is between 0.001 and 0.1M and by simultaneously or afterward bringing the pH to between 5 and 8 favoring the reticulation of the collagen chains.

The collagenic solutions treated with periodic acid or its salts may be used to prepare fibers, powders, microspheres or films, etc. by already known procedures, the mechanical characteristics of which would be improved and to which may be associated biologically active molecules.

As previously indicated, the treatment with periodic acid or its salts may equally be performed on already constituted gels in order to make them more stable.

In this regard, it should be noted that periodic acid or its salts, due to their small molecular size, diffuse easily into the interior of a gel and assure a homogenous reticulation.

The gel is treated by a solution of periodic acid or its salts, the concentration of which is advantageously between $10^{-1}$ and $10^{-4}$M, at a pH above 5 chosen in such a manner as to avoid a redissolution of the gel before the reaction, for 3 to 20 hours at ambiant temperature.

It is equally possible to perform the treatment conforming to the invention on films or powders in order to make them more stable or to create reactive groups on the surface for subsequent bonding.

These collagen films or powders are treated by a solution of periodic acid or of its salts, the concentration of which is between 0.1 and 0.0001M under pH conditions where the film or the material remains insoluble before the second step of pH 5 to 8 which favors reticulation leading to greater insolubility.

In general, it is advantageous to use the treatment conforming to the invention whenever it would be desireable to improve the stability and the mechanical characteristics of a cross-linked collagen and/or to associate the collagen with a biologically active molecule.

Other advantages and particularities of the invention will appear in the reading of the following examples which illustrate various possible embodiments of the invention.

Example 1 illustrates the preparation of an implant or of a lens from a collagen solution, the periodate treatment being carried out, in this example, on an already constituted gel.

Example 2 illustrates the preparation of an implant or of a lens from a collagen solution, the periodate treatment being carried out on the collagen solution.

Examples 3 and 4 illustrates the preparation of an implant or of a lens from a collagen solution where the periodate treatment is completed by a surface curing by a solution of sodium periodate or of glutaraldehyde.

Examples 5 and 6 refer to the preparation of an insoluble collagen gel from a collagen solution previously treated with periodate.

Example 7 refers to the preparation of an insoluble collagen gel associated with a biologically active molecule (fibronectin).

Examples 8 to 10 refer to the preparation of insoluble collagen fibers from collagen solutions treated with periodate, associated with a biologically active molecule (fibronectin).

Example 11 relates to the preparation of an insoluble powder from a collagen solution treated with periodate.

Example 12 refers to the preparation of an insoluble collagen powder from a collagen solution previously treated with periodate and to which is associated with a biologically active molecule (fibronectin or glycosaminoglycan).

Example 13 describes to the preparation of an insoluble collagen film from a collagen solution treated with periodate.

Example 14 illustrates to the preparation of insoluble collagen spheres from a collagen solution treated with periodate.

Examples 15 and 16 refer to the preparation of insoluble gels, films, fibers or spheres from a collagen solution treated with periodate, and associated with a biologically active molecule (glycosaminoglycan).

Example 17 illustrates the procedure for the treatment of a collagen powder by periodate.

EXAMPLE 1

An acid solution of human placental collagen, 15% Type IV enriched, in distilled water is prepared by the following process:

300 kg of placenta are ground in a frozen form to give pieces of a few cm$^3$ then mixed with 300 l of an aqueous solution containing 6 g/l of sodium chloride, 8% ethanol and 10 kg cellulose. After stirring at 10° C., the mixture is put through a MABILLE press to separate the blood from the placental tissue thus obtaining 102 kg of placental tissue containing 65% water.

The tissue removed from the press is stirred in 500 l of 0.05M sodium citrate at a pH of 7.2 for 30 min. at 10° C. then put through a press to eliminate the washing solution and to recover the tissue. A second washing is carried out with 500 l of the same solution to which has been added 30 g/l NaCl. A third washing is carried out with 500 l of 0.05M sodium citrate at pH 7.2. The tissue thus washed at a neutral pH is then subjected to three successive sequences of washings at acid pH, still at 10° C.:

by 500 l of 0.05M citric acid at a final pH adjusted to 2.8 by addition of 2N HCl; stirred for 30 minutes before the pressing operation;

by 500 l of 0.5M formic acid for 15 hours;

by 500 l of 0.05M citric acid to which 20 g/l NaCl has been added, for 30 min.

The placental tissue thus washed at an acid pH looks white, showing a good elimination of the initial placental blood pigments. The weight obtained is 82 kg.

The tissue is subjected to enzymatic digestion using 300 g of pepsin in 500 l of 0.05M citric acid at a pH of 2.8 for 15 hours at +10° C.

The suspension is then diluted by addition of 500 l water at +10° C. and the pH adjusted to 7.5 by addition of 4N NaOH, to denature the pepsin and suppress the protease action. After waiting 15 hours at +10° C., the tissue residue which still contains the essential part of the undissolved collagens I and III, is separated by a continuous centrifuge (WESTFALIA KG 10006). The weight of this residue is 103 kg; it may be subjected to a second, identical enzymatic digestion, followed by the extraction and separation of each of the collagens I and III according to the procedures described in the literature.

The supernatant corresponding to the first enzymatic digestion contains the essential part of the collagens and other macromolecules soluble at neutral pH after the action of pepsin. In particular, it contains Type IV collagen.

The pH of the supernatant is adjusted to 5 with 2N HCl and after waiting 15 hours at 10° C., the precipitate formed is eliminated by continuous centrifugation in a "BACTOFUGE" ALFA LAVAL centrifuge.

The pH of the supernatant, which is limpid, is adjusted to 7.5 by addition of NaOH and to a final concentration of 1.2M in NaCl. After 15 hours at 16° C., the precipitate of collagen formed is recovered by continuous centrifugation in a "Bactofuge".

The 13 kg of precipitate obtained is then dissolved in 600 l of 0.01N HCl and then the pH adjusted to 7.5 by addition of 4N NaOH. The precipitate formed after 15 hours at +4° C., is eliminated by "Bactofuge" centrifugation (weight obtained 10 kg).

The clear supernatant is acidifed to a pH of 2.8 with 2N HCl, and NaCl added to a final concentration of 0.6M at 4° C.

After 15 hours, the precipitate of collagen is collected by "Bactofuge" centrifugation. The precipitate, weighing 6.5 kg, has a fluid appearance. To it is slowly added 7 l of acetone, which provokes the formation of collagen fibers which are recovered by filtration through a sieve. The washing of these fibers with several acetone treatments, permits, after being dried under a flow of lukewarm sterile air, the obtaining of 180 g of dry fibers of the final product.

Dissolving these collagen fibers in water gives an acid solution.

This solution, brought to 15% is distilled water, is heated to 45°–60° C. for 30 minutes. The perfectly homogenous and fluid solution is filtered on membranes of a porosity of between 0.8 and 8 microns at this same temperature and poured into a mold, pre-heated to 45°–60° C., for the forming of lenses or ophthalmic implants. The entire assembly is immediately chilled to +4° C. for 15 hours. After unmolding, the lens or implant is put into a solution of 0.01M sodium periodate at a pH of 7.5 for 15 hours at ambiant temperature. Then the lens or implant is transferred into a 20 g/l glycine buffer, pH 7.5, or 0.05M ethanolamine and/or into a solution of 0.02M sodium hydroboride for 3 hours at ambiant temperature.

The implants or lenses obtained are perfectly transparent, very flexible and very water absorbent and prove to be of an easy manipulability, being stronger mechanically and of a great stability, resisting a thermal treatment at 95° C. for one hour in a buffer at neutral pH, while a lens or implant not treated with sodium periodate is very rapidly hydrolyzed.

EXAMPLE 2

To a perfectly homogenous and fluid acid solution of collagen at 15% from Example 1, is added a solution of periodic acid up to a final concentration of 0.0001M. After being homogenized and the bubbles eliminated, the solution is poured into a mold pre-heated to 45°–60° C. The entire assembly is immediately chilled to +4° C. for 15 hours.

Once unmolded, the lens or implant is put into a 10 g/l NaCl, 0.01M phosphate buffer at a pH of 7.5 for 15 hours then into a 20 g/l glycine buffer, pH 7.5, or 0.05M ethanolamine and/or into a solution of 0.02M sodium hydroboride for 3 hours at ambiant temperature.

The lens or implant has the same characteristics as those described in Example 1.

EXAMPLE 3

The lens or implant prepared according to Example 2, once unmolded, is put into a solution of 0.01M sodium periodate at a pH of 7.5 for 15 hours at ambiant temperature, then into a 20 g/l glycine buffer, 10 g/l NaCl, pH 7.5, or 0.05M ethanolamine and/or into a solution of 0.02M sodium hydroboride for 3 hours at ambiant temperature.

The lens or implant has the same characteristics as those described in Example 1.

EXAMPLE 4

The lens or implant prepared according to Example 2, once unmolded, is put into a solution of 0.2% glutaraldehyde at a pH of 7.5 for 15 hours at ambiant temperature, then into a 20 g/l glycine buffer, 10 g/l NaCl, pH 7.5, or 0.05M ethanolamine and/or into a solution of 0.02M sodium hydroboride for 3 hours at ambiant temperature.

EXAMPLE 5

A solution of human collagen (Type III, I or IV) or acid bovine collagen (Type I) at 0,2% in distilled water is treated with 0.001M sodium periodate for 2 hours at ambiant temperature. The solution is then dialyzed against 0.01N hydrochloric acid for 20 hours.

The pH of the solution is then adjusted to 7.5 by addition of 0.1N NaOH; after 10 min. at ambiant temperature, a gel has been formed which, after washing with glycine or ethanolamine buffers and equilibration with a culture medium, may be used for cell culture or as a product for the filling of wounds.

Thus at ambient temperature, very stable gels have been obtained which resist extremes of pH (0.01HCl) and are very easily manipulated. These gels are obtained equally well with acid-soluble collagens or with those dissolved by enzyme or alkaline treatment with or without telopeptides.

EXAMPLE 6

A volume/volume mixture of oxidized collagen according to Example 5, and normal collagen at 0.6% in distilled water, the pH of which is adjusted to 7.5 with 0.1N NaOH, forms into a gel in 10 min. at ambiant temperature.

EXAMPLE 7

A mixture of: 1 volume oxidized collagen according to Example 5, 1 volume normal collagen at 6% in distilled water, 0.2 volume 10 g/l plasma fibronectin sets to a gel in 10 min. at ambiant temperature and at neutral pH. The proportions of the different reagents may be largely modified to include more fibronectin if necessary.

EXAMPLE 8

A solution of oxidized collagen according to Example 5 is poured, under agitation, into a 0.04M phosphate buffer, pH 7.2 at 37° C. It immediately forms tiny (fibrils) of collagen. After 2 hours, these fibrils are washed in glycine or ethanolamine buffer and/or with a solution of 0.02M sodium hydroboride for 3 hours at ambiant temperature.

These very stable small fibers do not redissolve in an acid medium and may be used as a product for filling wounds or for the adsorption or proteins (fibronectin, etc. . . . ).

EXAMPLE 9

The mixtures of Examples 6 and 7 are poured, under agitation, into a 0.04M phosphate buffer, pH 7.2 at 37° C. Fibrils of collagen are immediately formed. After 2 hours, these fibrils are washed in glycine buffer or ethanolamine and/or with a solution of 0.02M sodium hydroboride for 3 hours at ambiant temperature.

EXAMPLE 10

A solution of oxidized collagen according to Example 5 is poured into 0.01 g/l plasma fibronectin in 0.04M phosphate buffer, pH 7.5. It immediately forms tiny fibers of collagen incorporating the plasma fibronectin.

EXAMPLE 11

A solution of oxidized collagen according to Example 5 is adjusted to a pH of 3 then a sodium chloride solution is added to a 1M final concentration. After 15 hours, it is centrifuged to recover a precipitate which, after dehydration with 100% acetone, drying under a flow of air, and grinding, gives a powder of insoluble collagen having reactive groups suitable for subsequent bonding or for use as a bone filter.

EXAMPLE 12

A solution of oxidized collagen according to Example 5 is adjusted to a pH of 4 after which 0.01 g/l plasma fibronectin and/or 0.1% glycosaminoglycan is rapidly added. After 2 hours of contact, a sodium chloride solution is added to 1M final concentration. After 15 hours, it is centrifuged to recover a very solid precipitate which may be used to repair tissue lesions.

EXAMPLE 13

Glycerine (1.5% final concentration) is added to the solution of oxidized collagen according to Example 5 or to the mixture used in Example 6, the result is poured onto a water-repellent surface. After drying at ambiant temperature under a flow of sterile air, a film is obtained. After 30 min. treatment in 95% alcohol then dehydration in a bath of 100% acetone, an insoluble film is obtained, the flexibility, thickness and resistance of which may vary as a function of the concentration in collagen and in glycerine.

EXAMPLE 14

The solution of oxidized collagen according to Example 5 or the mixture used in Example 6 is introduced drop by drop into a mixture of 9 volumes of acetone and 1 volume of 0.1N NaOH. Each droplet jells immediately and definitively retains its spherical shape. The suspension obtained is then washed by a sterile physiologic solution to eliminate the acetone and to neutralize the pH in a definitive manner.

The spheres thus obtained may be used in cell culture. Of course, other procedures may be used to obtain large quantities of collagen micro-spheres. In particular, all the known processes for preparing emulsions of microdroplets may be used.

EXAMPLE 15

1 volume oxidized collagen according to Example 5, 1 volume of 0.1% glycosaminoglycan (chondroitin 6 sulfate or chondroitin 4 sulfate, heparan sulfate, dermatan sulfate, hyaluronic acid), the pH of which has been adjusted to 7.5 with 0.1N NaOH may be used to make gels, fibers or spheres.

EXAMPLE 16

A solution of 0.5% oxidized collagen is mixed volume for volume with a solution of 0.2% glycosaminoglycan, the pH adjusted to 7.5 and the mixture immediately poured into a mold in such a manner as to achieve a thickness of around 1 cm. After 2 hours at ambiant temperature, the sheet is frozen and lyophilized to obtain compresses which are more resistant to biodegradation and may be used as a product for healing gaps.

EXAMPLE 17

A saline precipitate of collagen, after dehydration in acetone, drying under a flow of air, and grinding, gives a powder.

This latter is added (0.2%) to a solution of 0.001M $NaIO_4$ in 95% alcohol. After 2 hours of contact under stirring at ambiant temperature, the powder is washed on a nylon cloth in 95% alcohol then 100% acetone before being dryed under a flow of air and grinding.

These powders, having become insoluble, react with Schiff's reagent. Collagen powder without telopeptide (Trillagène, sold by SADUC) remains soluble in water and jells as soon as the pH of the solution is adjusted to 7.5.

These powers thus obtained and the powder obtained in Example 11, which are insoluble, are mixed with a nonoxidized collagen and/or glycosaminoglycans and/or antibiotics to form a homogenous paste useable as a bonefilling product.

We claim:

1. A process for reticulating collagen and permitting the obtaining of a reticulated collagen with improved stability and mechanical characteristics, comprising submitting a non-reticulated collagen to a controlled oxidation by treatment with a solution of periodic acid or of a periodate.
2. The process according to claim 1, wherein it is carried out on a collagen solution.
3. The process according to claim 1, wherein it is carried out on an already constituted collagen gel.
4. The process according to claim 1, wherein it is carried out on collagen in the form of powders or films.
5. The process according to claim 1, wherein, when it is applied to the preparation of a gel, a solution of sodium periodate, up till a concentration of $10^{-1}$ to $10^{-4}$M is obtained, is added to the collagen solution, the pH being between 2 and 8.
6. The process according to claim 5, wherein the treatment is carried out in two stages, the first at an acid pH and the second at a neutral or basic pH.
7. The process according to claim 1, wherein the already constituted gel is treated with a solution of sodium periodate at a concentration of between $10^{-1}$ to $10^{-4}$M, at a pH, at least in the second stage, of between 5 and 8, for 3 to 20 hours at ambiant temperature.
8. The process according to claim 1, wherein collagen powders or films are treated with a solution of sodium periodate at a concentration of between $10^{-1}$ to $10^{-4}$M, at a pH of between 5 and 8, for 3 to 20 hours at ambiant temperature.
9. The process according to claim 1, wherein it may be followed by a washing or neutralization step.
10. The process according to claim 9, wherein the washing is carried out using a solutin of glycine.
11. The process according to claim 9, wherein the washing is carried out using a solution of ethanolamine.
12. The process according to claim 9, wherein the washing is carried out using a solution of sodium hydroborate.
13. The process according to claim 1, wherein it may be followed by a surface curing.
14. The process according to claim 13, wherein the surface curing is carried out using a solution of sodium periodate.
15. The process according to claim 13, wherein the surface curing is carried out using a solution of di- or polyaldehyde.
16. The process according to claim 13, wherein the surface curing is carried out using a solution of sodium periodate the concentration of which is between $10^{-1}$ to $10^{-4}$M, at a pH of between 5 and 8, for 3 to 20 hours.
17. The process according to claim 13, wherein the surface curing is carried out using a solution of di- or polyaldehyde the concentration of which is between 0.1 and 0.001M, at a pH of between 5 and 8, for 3 to 20 hours.
18. An application of the collagenic solutions treated by the process according to claim 1, to the preparation of powders, fibers, spheres or films.
19. A collagen gel with improved stability and mechanical characteristics, wherein it is obtained by application of the process according to claim 1.
20. A reticulated collagen in the form of powders or gels, with improved stability and mechanical characteristics, wherein it is subjected to a treatment according to claim 1.

21. A collagen gel with reactive groups useable for subsequent bonding, wherein it is obtained by application of the process according to claim 1.

22. A collagen in the form of powders or gels with reactive groups useable for subsequent bonding, wherein it is obtained by application of the process according to claim 1.

23. Process according to claim 1 wherein the controlled oxidation is carried out by treatment with a solution of sodium periodate.

24. Collagen gel according to claim 22, wherein the reactive groups are linked to biologically active molecules permitting a better biocompatibility and a greater resistance to biodegradation.

25. Collagen gel according to claim 24, wherein the biologically active molecules are selected from proteins, fibronectin, growth factors, glycosaminoglycans, enzymes, bacteriocidal or bacteriostatic agents and antibiotics.

26. Collagen in the form of powders or gels according to claim 22, wherein the reactive groups are linked to biologically active molecules as defined in claim 23.

* * * * *